(12) United States Patent
Govari

(10) Patent No.: US 11,166,645 B2
(45) Date of Patent: Nov. 9, 2021

(54) VISUALIZING LESIONS FORMED BY THERMAL ABLATION IN A MAGNETIC RESONANCE IMAGING (MRI) SCAN

(71) Applicant: Biosense Webster (Israel) Ltd., Yokneam (IL)

(72) Inventor: Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 307 days.

(21) Appl. No.: 16/223,351

(22) Filed: Dec. 18, 2018

(65) Prior Publication Data

US 2020/0187821 A1 Jun. 18, 2020

(51) Int. Cl.

| A61B 5/055 | (2006.01) |
|---|---|
| A61B 90/00 | (2016.01) |
| A61B 34/10 | (2016.01) |
| A61B 5/00 | (2006.01) |
| A61B 18/18 | (2006.01) |
| A61B 18/20 | (2006.01) |
| A61B 18/00 | (2006.01) |
| G01R 33/56 | (2006.01) |

(52) U.S. Cl.
CPC .............. *A61B 5/055* (2013.01); *A61B 90/37* (2016.02); *A61B 5/0035* (2013.01); *A61B 18/1815* (2013.01); *A61B 18/20* (2013.01); *A61B 34/10* (2016.02); *A61B 2018/00791* (2013.01); *A61B 2090/374* (2016.02); *A61B 2090/3954* (2016.02); *G01R 33/56* (2013.01)

(58) Field of Classification Search
CPC ......... A61B 5/055; A61B 90/37; A61B 34/10; A61B 2090/374; A61B 2090/3954; A61B 5/0035; A61B 18/1815; A61B 18/20; A61B 2018/00791; A61B 5/0044; A61B 18/1492; A61B 34/20; A61B 2576/023; A61B 2018/00577; A61B 2034/2051; G01R 33/56; G06T 2207/30048; G06T 7/74; G06T 2200/04; G06T 2207/10088; G06T 2207/30096; G06T 7/0014; G06T 5/002; G06T 7/11; G06K 9/6202
See application file for complete search history.

(56) References Cited

U.S. PATENT DOCUMENTS

| 5,003,979 A | 4/1991 | Merickel |
| 5,391,199 A | 2/1995 | Ben-Haim |

(Continued)

OTHER PUBLICATIONS

Extended European Search Report dated Feb. 18, 2020 for the European Patent Application No. 19217071.0.

(Continued)

*Primary Examiner* — Christopher Koharski
*Assistant Examiner* — Kaitlyn E Selmer
(74) *Attorney, Agent, or Firm* — Volpe Koenig

(57) ABSTRACT

A magnetic resonance imaging (MRI) visualization method includes identifying a location of a thermally induced lesion in an MRI image by deriving a spatial pattern of MRI pixel values, which represents the lesion as it is expected to appear in the MRI image, as a function of thermal energy applied in creating the lesion. The MRI image is matched with the spatial pattern of pixel values. A local maximum value is found in the matched MRI image, and a location of the local maximum value is presented in the matched MRI image as the location of the lesion.

11 Claims, 3 Drawing Sheets

(56) References Cited

U.S. PATENT DOCUMENTS

| | | |
|---|---|---|
| 5,443,489 A | 8/1995 | Ben-Haim |
| 5,558,091 A | 9/1996 | Acker et al. |
| 5,944,022 A | 8/1999 | Nardella et al. |
| 5,983,126 A | 11/1999 | Witkampf |
| 6,172,499 B1 | 1/2001 | Ashe |
| 6,177,792 B1 | 1/2001 | Govari et al. |
| 6,310,447 B1 | 10/2001 | Schneider |
| 6,310,477 B1 * | 10/2001 | Schneider .......... G01R 33/4822 324/307 |
| 6,456,864 B1 | 9/2002 | Swanson et al. |
| 6,690,963 B2 | 2/2004 | Ben-Haim et al. |
| 6,788,967 B2 | 9/2004 | Ben-Haim et al. |
| 9,846,765 B2 | 12/2017 | Audieger et al. |
| 2005/0038619 A1 | 2/2005 | Degani |
| 2010/0021031 A1 | 1/2010 | Brockway et al. |
| 2011/0251607 A1 * | 10/2011 | Kruecker .......... A61B 18/1206 606/34 |
| 2012/0027278 A1 | 2/2012 | Chaney et al. |
| 2014/0136174 A1 * | 5/2014 | Audigier ................ G09B 23/30 703/11 |
| 2018/0240233 A1 * | 8/2018 | Kiraly .................. G06T 7/0012 |

OTHER PUBLICATIONS

Wu et al., "Atrial Fibrosis Quantification Based on Maximum Likelihood Estimator of Multivariate Images," In: Frangi A., Schnabel J., Davatzikos C., Alberola-López C., Fichtinger G. (eds) Medical Image Computing and Computer Assisted Intervention—MICCAI 2018. MICCAI 2018. Lecture Notes in Computer Science, vol. 11073. Springer, Cham (2018).

Orczyk et al., "3D Registration of mpMRI for Assessment of Prostate Cancer Focal Therapy," Acad Radiol., 24 (12): 1544-1555 (2017).

Breen et al., "Image-guided laser thermal ablation therapy: a comparison of modeled tissue damage using interventional MR temperature images with tissue response," Proc. SPIE 5367, Medical Imaging 2004: Visualization, Image-Guided Procedures, and Display, (May 5, 2004).

* cited by examiner

VISUALIZING LESIONS FORMED BY THERMAL ABLATION IN A MAGNETIC RESONANCE IMAGING (MRI) SCAN

FIELD OF THE INVENTION

The present invention relates generally to medical magnetic resonance imaging (MRI), and particularly to cardiac MRI.

BACKGROUND OF THE INVENTION

Various techniques for improving the diagnostic value of an MRI image have been proposed in the patent literature. For example, U.S. Pat. No. 5,003,979 describes an image processing, pattern recognition and computer graphics system and method for the noninvasive identification and evaluation of female breast cancer including the characteristic of the boundary thereof using multidimensional Magnetic Resonance Imaging (MRI). The system and method classify the tissue using a Fisher linear classifier followed by a refinement to show the boundary shape of the carcinoma. The results are a high information content display which aids in the diagnosis, and in the analysis of the size of the carcinoma.

As another example, U.S. Patent Application Publication 2012/0027278 describes methods, systems, and computer readable media for mapping a model of an object comprising an anatomical structure in a planning image and an intervention target region within it to intervention-guiding image data. According to one method, an initial medial representation object model (m-rep) of an object comprising an anatomical structure is created based on image data of at least a first instance of the object. An m-rep may be created based on one or more pre-biopsy MR images of an object. A patient-specific m-rep is created by deforming the initial m-rep based on planning image data of at least a second instance of the object, wherein the at least second instance of the object is associated with the patient. An intervention target region within the m-rep is identified in an image registered with the planning image. The patient-specific m-rep is correlated to the intervention-guiding image data of the at least second instance of the object, deformed from the planning image. The intervention target region is transferred to the intervention-guiding image according to the transformation between the m-rep in the planning image and the m-rep in the intervention-guiding image.

U.S. Pat. No. 6,310,477 describes a three-dimensional (3D) MR image, acquired before injection of a contrast agent, and an enhanced 3D MR image that is acquired after injection of the contrast agent. The two images are registered and then subtracted to remove background and to highlight lesion voxels. Lesion objects are identified by connecting contiguous lesion objects. Volume and surface area of any continuous lesion object in a discrete digital image are then calculated. Malignant lesions are identified by determining the ratio of volume to surface area for each lesion object. Malignant tumors are identified when this ratio drops below a preset threshold.

U.S. Patent Application Publication 2010/0021031 describes a method of processing regions of interest (ROI) obtained using computer-aided detection (CAD) along with reference image data to assist in evaluation of disease within an anatomical volume. After obtaining ROIs and reference image data, additional information related to each ROI is automatically computed. Subsets of ROIs are selected for use in visualization. ROIs are then presented to an observer in interactive, linked views, each view presenting optimally certain aspects of the ROIs and mapping ROI inclusion within the subsets to visual parameters. The disclosed method may be applied to MRI images.

SUMMARY OF THE INVENTION

An embodiment of the present invention provides a magnetic resonance imaging (MRI) visualization method, including identifying a location of a thermally induced lesion in an MRI image by deriving a spatial pattern of MRI pixel values, which represents the lesion as it is expected to appear in the MRI image, as a function of thermal energy applied in creating the lesion. The MRI image is matched with the spatial pattern of pixel values. A local maximum value is found in the matched MRI image, and a location of the local maximum value is presented in the matched MRI image as the location of the lesion.

In some embodiments, deriving the spatial pattern of MRI pixel values includes solving a model of the thermally induced lesion, and transforming the solved model into the spatial pattern of pixel values.

In some embodiments, deriving the spatial pattern of MRI pixel values further includes normalizing the spatial pattern of pixel values.

In an embodiment, matching the MRI image with the spatial pattern of pixel values includes convolving the MRI image with the spatial pattern of pixel values. In another embodiment, matching the MRI image with the spatial pattern of pixel values includes matching a segmented region of the MRI image.

In some embodiments, the visualization method further includes saving the MRI image with the identified location overlaid on the image.

In some embodiments, the visualization method further includes saving the matched MRI image in a memory.

There is additionally provided, in accordance with an embodiment of the present invention, a system for magnetic resonance imaging (MRI) visualization, the system including a processor and a memory. The processor is configured to identify a location of thermally induced lesion on an MRI image by (a) deriving a spatial pattern of MRI pixel values, which represents the lesion as it is expected to appear in the MRI image, as a function of thermal energy applied in creating the lesion, (b) matching the MRI image with the spatial pattern of pixel values, and (c) finding a local maximum value in the matched MRI image. The memory is configured to store the MRI image with a location a location of the local maximum value marked thereon as the location of the lesion.

The present invention will be more fully understood from the following detailed description of the embodiments thereof, taken together with the drawings in which:

DETAILED DESCRIPTION OF EMBODIMENTS

Overview

Figure 1:
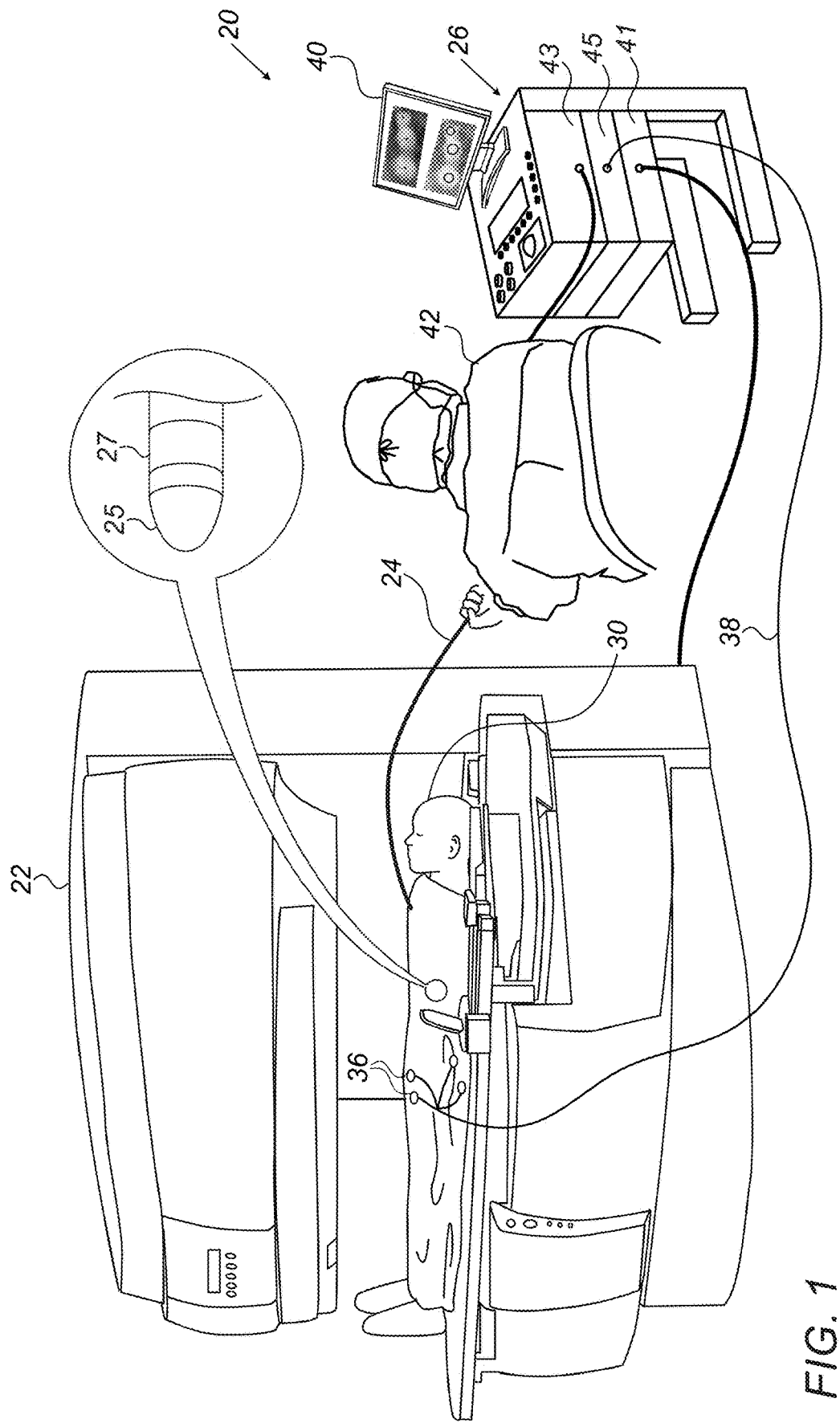
FIG. 1 is a schematic, pictorial illustration of a magnetic resonance imaging (MRI)-guided ablation system, in accordance with an embodiment of the present invention.

Magnetic resonance imaging (MRI) images typically comprise grayscale pixels that represent different tissue properties and compositions. During and after thermal ablation, such as radiofrequency (RF) ablation of tissue, due to the production of a lesion, a change occurs in grayscale value of such tissue in MRI images. However, the change may be small and/or it may be masked by other effects, such as motion artifacts and image noise, which causes difficulty in MRI visualization of a lesion, such as a cardiac lesion.

Embodiments of the present invention that are described hereinafter provide methods and systems that identify and visualize a location of a thermally induced lesion. In some embodiments, the location of the lesion is identified by matching, for example by convolving, a normalized spatial pattern of MRI pixel values with the MRI image over different cardiac positions within the image. The spatial pattern of MRI pixel values represents the lesion as it is expected to appear in the MRI image. A pixel position with the highest convolution value corresponds to a center position in the convolved MRI lesion image, since the convolution reduces the noise effects in the MRI image. The user may save the uploaded MRI image with the visualized lesion location overlaid on the image in a memory, for future use.

In some embodiments, the normalized spatial pattern of MRI pixel values is derived by: (a) solving a thermally induced lesion model, (b) transforming the solution into a spatial pattern of MRI pixel values, as described below, and (c) normalizing the spatial pattern of MRI pixel values.

In an optional embodiment, surrounding convolved positions result in the appearance of a shape of the lesion in the convolved MRI image. The disclosed technique may therefore further improve the MRI lesion visualization by generating, using the convolution, a lesion-enhanced MRI image, as described below. In some embodiments, a model of expected change in pixel values of an imaged lesion as a function of the deposited thermal energy is provided. The disclosed method provides a normalized spatial pattern of MRI pixel values, (i.e., a calculated weighting distribution).

The disclosed method assumes that MRI pixel values of a lesion are a monotonic function of the deposited thermal energy (i.e., that a visual property of tissue imaged by MRI, such as a pixel value of an ablated tissue, varies monotonically with the deposited ablative energy). One or more equations describing an ablation-induced pixel MRI function are constructed based on heat propagation assumptions, using parameters such as irrigation rate for cooling tissue surface, RF current density, and heat conductivity of blood and tissue. The disclosed model (i.e., the one or more abovementioned equations) is then solved using a processor, and a resulting solution is transformed, as described below, into pixel values and then normalized to produce the weighting function.

In an embodiment, the convolution is performed within regions of the MRI image where lesions are expected, so as to reduce computation time and to avoid generating artifacts (e.g., wrongly identifying unrelated features as lesions). To define such regions, the MRI image may be initially segmented by a processor running dedicated software and/or manually segmented by a user.

The processor is programmed in software containing a particular algorithm that enables the processor to conduct each of the processor related steps and functions outlined above.

The disclosed technique enhances the visualization in an MRI image of a lesion formed by ablation, and may therefore improve the diagnostic value of the MRI image.

System Description

FIG. 1 is a schematic, pictorial illustration of a magnetic resonance imaging (MRI)-guided ablation system 20, in accordance with an embodiment of the present invention. System 20 comprises an MRI scanner 22, configured to image a patient 30 while a physician 42 performs an ablation procedure. System 20 further comprises a processor 41, located, for example, in a console 26. During the procedure, processor 41 controls the image acquisition by the MRI scanner, as described in detail hereinbelow.

To perform the ablation, physician 42 uses an ablation catheter 24. Typically, catheter 24 comprises an ablation electrode 25, and further comprises a tracking sensor 27, which outputs tracking signals that indicate the location and orientation of the catheter inside the body of patient 30. For example, tracking sensor 27 may comprise a magnetic sensor. During the procedure, one or more magnetic-field generators (not shown) may generate magnetic fields at different frequencies from those generated by the MRI scanner, which induce voltages in sensor 27. These induced voltages are received, by processor 41, via an electrical interface 43. Based on the induced voltages, the processor ascertains the location and orientation of the catheter. Such magnetic tracking techniques are described, for example, in U.S. Pat. Nos. 5,391,199, 5,443,489, 6,788,967, 6,690,963, 5,558,091, 6,172,499, and 6,177,792, whose disclosures are incorporated herein by reference.

Alternatively or additionally, system 20 may comprise any other type of sensor which may be used to implement any other suitable tracking technique for tracking the location and/or orientation of the catheter. For example, impedance sensors may be used to implement an impedance-based tracking technique, as described, for example, in U.S. Pat. Nos. 5,983,126, 6,456,864 and 5,944,022, whose disclosures are incorporated herein by reference.

System 20 further comprises one or more body surface electrodes 36, which output electrocardiogram (ECG) signals that indicate the phase of the cardiac cycle of patient 30 at which the tracking signals are acquired. The ECG signals are conveyed, via a cable 38 and an ECG interface 45, to processor 41. Alternatively or additionally, processor 41 may receive intracardiac ECG signals acquired by ECG sensors in catheter 24.

During the procedure, images acquired by the MRI scanner may be displayed on a display 40, to help guide the physician.

Processor 41 is typically a general-purpose computer programmed in software to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 41 runs a dedicated algorithm that enables processor 41 to perform the disclosed steps as further described below.

Seeing Lesions Formed by Thermal Ablation in an MRI Scan

Figure 2A:
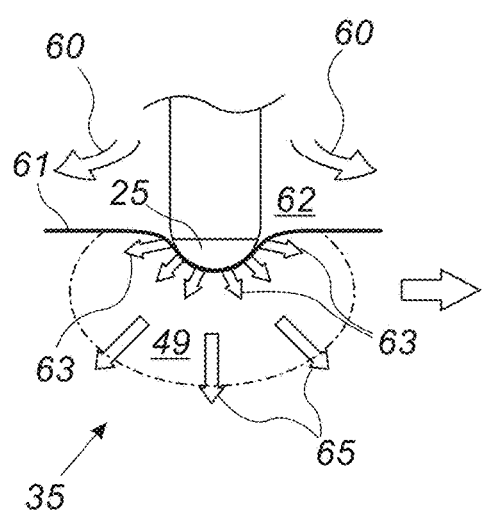
FIGS. 2A and 2B are schematic, pictorial illustrations of an RF induced lesion model and resulting normalized spatial pattern of MRI pixel values, in accordance with an embodiment of the present invention.
Figure 2B:
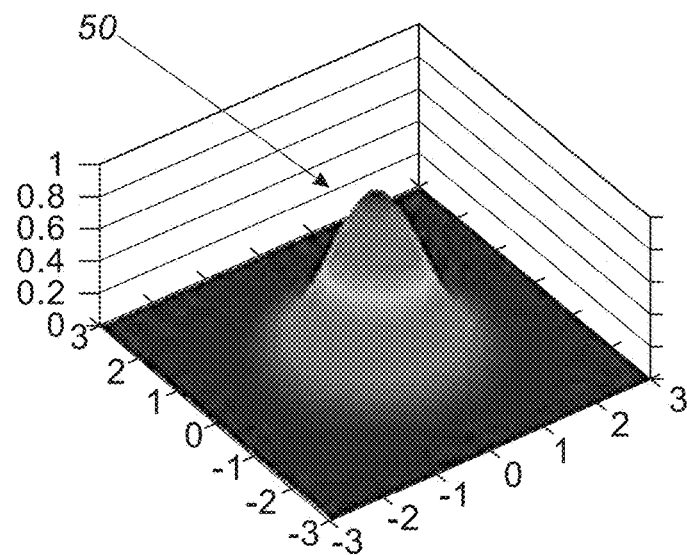

FIGS. 2A and 2B are schematic, pictorial illustrations of an RF induced lesion model 35 and resulting normalized spatial pattern of MRI pixel values 50, in accordance with an embodiment of the present invention.

Model 35 is based on heat propagation assumptions. The heat source comprises joule heating due to RF currents 63 that are injected by electrode 25 into tissue 49. The model may assume that RF current density falls with distance from electrode 25, as in an inverse $r^2$ model, or it may use a more refined model of the drop of current density. Cooling irrigation flow 60 cools tissue surface 61 and blood 62, while current heat conductivity of the tissue causes a heat propagation 65 deeper into tissue 49. A solution S(r) of model 35 yields a three-dimensional distribution (i.e., function) of the thermal energy deposited into tissue 49 as a result of the RF ablation.

An example of a heat-equation-based tissue necrosis model is described in U.S. Pat. No. 9,846,765 in which, in an embodiment, a temperature map shows simulated heat diffusion in a target organ due to thermal ablation that is calculated and overlaid on a medical image of the organ. U.S. Pat. No. 9,846,765 disclosure is incorporated herein by reference. Alternatively, any other suitable model can be used.

The disclosed method further assumes pixel MRI values of a lesion to be a monotonic function of the deposited energy (i.e., a property of tissue being MRI imaged, such as composition, varies monotonically with the deposited ablative energy), as described below. In the context of this disclosure, this assumption is used to transform the solution of model 35 into a pixel MRI value function. The transformation may be done analytically or by a lookup table, which is derived, for example, empirically.

For example, a spatial pattern of pixel values, pV(r), may be an additive function of the solution, pV(r)=pV0(r)+α·S(r), where pV0(r) is the pixel value before ablation, and α is a fitted parameter. Alternatively, another suitable function or relation can be used.

By such a transformation and normalization, processor 41 calculates normalized spatial pattern of pixel values 50. The resulting function 50 is a weight function, with a maximal value of one, and typically drops as a function of radial distance (e.g., given in millimeters) from its maximum. As an example, however, in general when tissue properties are spatially heterogenous to a sufficient degree, the normalized spatial pattern of pixel values may not possess any symmetry property, and rather be a general function of a spatial vector r.

The example illustrations shown in FIGS. 2A and 2B are chosen purely for the sake of conceptual clarity. The shape of function 50 may vary based on changing assumptions of model 35, such as the heat conductivity of tissue.

Figure 3:
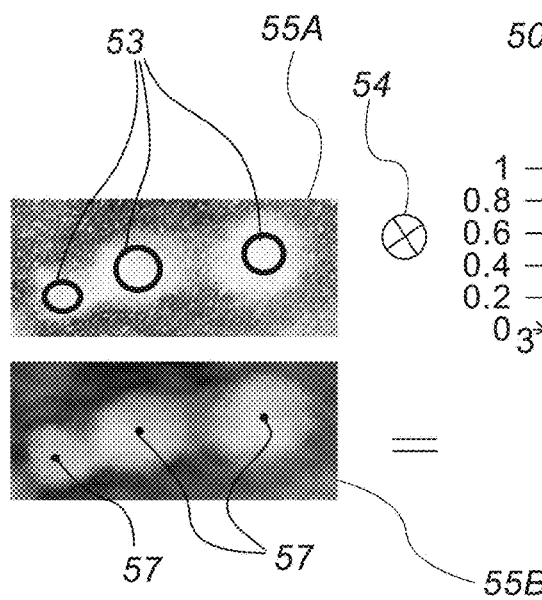
FIG. 3 is a schematic, pictorial illustration of enhanced lesion visibility in an MRI image after convolving the image with the function of FIG. 2, in accordance with an embodiment of the present invention.

FIG. 3 is a schematic, pictorial illustration of enhanced lesion visibility in an MRI image after convolving an MRI image with the function of FIG. 2, in accordance with an embodiment of the present invention. Due to image noise, there may be some uncertainty in the locations of lesions seen in region 55A within areas 53. Normalized spatial pattern of MRI pixel values 50 is convolved (54) with a region 55A of an MRI noisy image that shows lesions.

As seen, a resulting lesion-enhanced region 55B of the MRI image has accurately identified center locations 57 of the lesions. Locations 57 are local maxima of the MRI values of the convolved smooth (i.e., lower noise) image. As noted above, region 55A may be defined by performing segmentation on the respective MRI image, so as to avoid performing convolution with the entire image.

Optionally a convolved MRI image is generated (showing a reduced image noise and clearer delineation of lesion boundaries (i.e., a lesion enhanced image).

Figure 4:
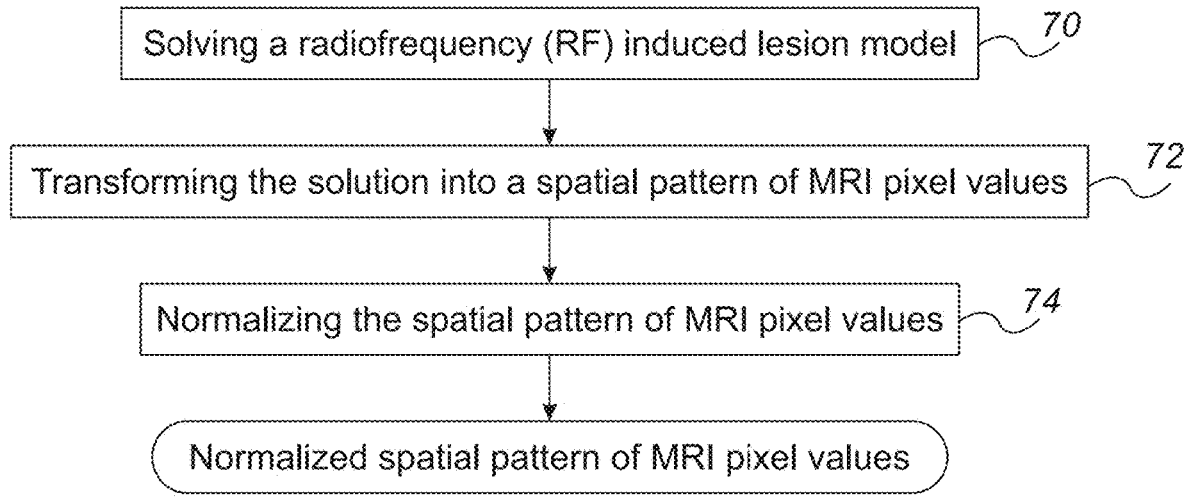
FIG. 4 is a flow chart that schematically illustrates a method for deriving the normalized spatial pattern of MRI pixel values of FIG. 2, in accordance with an embodiment of the present invention.

FIG. 4 is a flow chart that schematically illustrates a method for deriving normalized spatial pattern of MRI pixel values 50 of FIG. 2, in accordance with an embodiment of the present invention. The algorithm, according to the presented embodiment, carries out a process that begins with processor 41 solving a radiofrequency (RF) induced lesion model 35, at a model solving step 70. Next, processor 41 transforms the solution into a spatial pattern of pixel values, as described above, at a solution transformation step 72. Finally, processor 41 normalizes the spatial pattern of pixel values to obtain normalized spatial pattern of pixel values 50, at a normalization step 74.

The example flow chart shown in FIG. 4 is chosen purely for the sake of conceptual clarity. The present embodiment also comprises additional steps of the algorithm, such as approximations, which have been omitted from the disclosure herein purposely on order to provide a more simplified flow chart.

Figure 5:
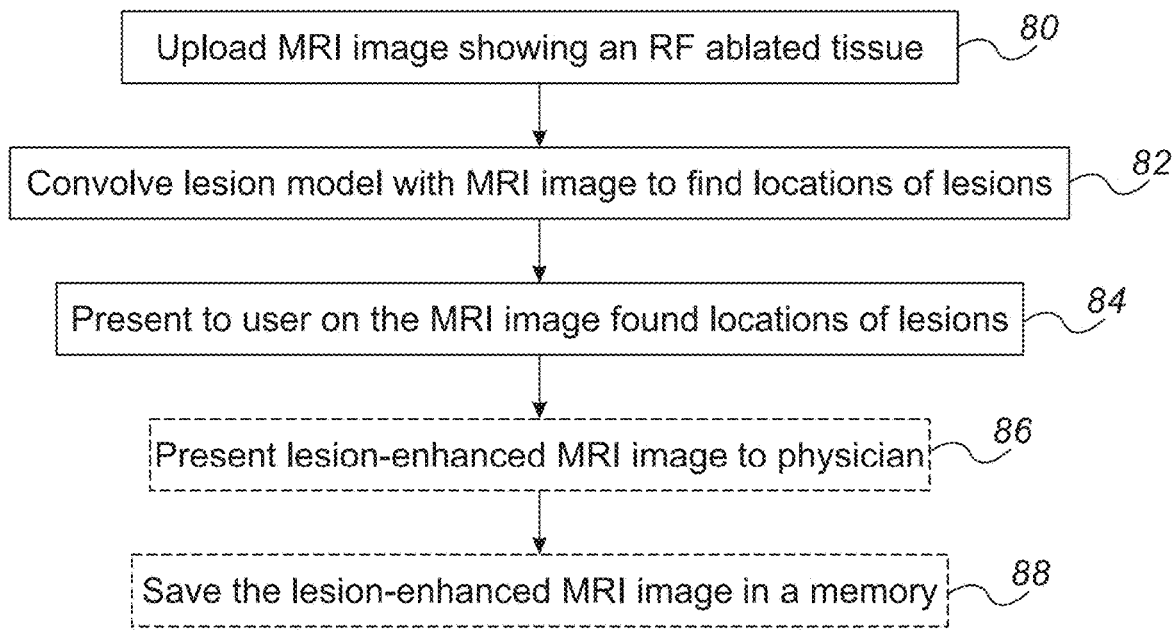
FIG. 5 is a flow chart that schematically illustrates a method for enhancing lesion visibility in an MRI image, in accordance with an embodiment of the present invention.

FIG. 5 is a flow chart that schematically illustrates a method for enhancing lesion visibility in an MRI image, in accordance with an embodiment of the present invention. The algorithm, according to the presented embodiment, carries out a process that begins with processor 41 uploading at least one MRI image that shows RF-ablated tissue (e.g., an image including region similar to region 55A), at an MRI image uploading step 80. Next, the model convolves normalized spatial pattern of pixel values 50 (i.e., applies the disclosed solved lesion model) with the uploaded MRI image, so as to accurately identify on the uploaded image center locations 57 of the lesions, at a lesion location finding step 82. Then, processor 41 presents to a user the uploaded MRI image with the found center locations (e.g., locations 57) of thermally induced lesions, at a lesion visualization step 84.

Optionally, processor 41 generates a lesion-enhanced MRI image and presents the lesion-enhanced MRI image (e.g., an image including region similar to region 55B) to the user, at a lesion-enhanced image presentation step 86. Finally, processor 41 may save the lesion-enhanced MRI image in memory, at a lesion-enhanced MRI image saving step 88.

The present embodiment also comprises additional steps of the algorithm, such as applying segmentation to the uploaded MRI image, which have been omitted from the disclosure herein purposely on order to provide a more simplified flow chart.

Although the embodiments described herein mainly address cardiac MRI applications, the methods and systems described herein can also be used in other applications, such as in MRI visualization of an RF ablated lesion in other organs. Moreover, the disclosed method may be implemented, with the necessary changes have been made, to the MRI visualization of lesions induced by other ablative methods, such as laser ablation, ultrasound ablation, or microwave ablation.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A magnetic resonance imaging (MRI) visualization method, the method comprising identifying a location of a thermally induced lesion in an MRI image by:
   deriving a spatial pattern of MRI pixel values, which represents the lesion as it is expected to appear in the MRI image,
   by calculating, using a predetermined formula, a model of the thermally induced lesion as a function of thermal energy applied in creating the lesion, and transforming the solved model into the spatial pattern of MRI pixel values;
   matching the MRI image with the spatial pattern of MRI pixel values;
   finding a local maximum value in the matched MRI image; and
   presenting a location of the local maximum value in the matched MRI image as the location of the lesion.

2. The visualization method according to claim 1, wherein deriving the spatial pattern of MRI pixel values further comprises normalizing the spatial pattern of pixel values after transforming the solved model.

3. The visualization method according to claim 1, wherein matching the MRI image with the spatial pattern of pixel values comprises convolving the MRI image with the spatial pattern of pixel values.

4. The visualization method according to claim 1, wherein matching the MRI image with the spatial pattern of pixel values comprises matching a segmented region of the MRI image.

5. The visualization method according to claim 1, and comprising saving the MRI image with the identified location overlaid on the image.

6. The visualization method according to claim 1, and comprising saving the matched MRI image in a memory.

7. A system for magnetic resonance imaging (MRI) visualization, the system comprising:
   a processor, which is configured to identify a location of a thermally induced lesion on an MRI image by:
      deriving a spatial pattern of MRI pixel values, which represents the lesion as it is expected to appear in the MRI image, calculating, using a predetermined formula, a model of the thermally induced lesion as a function of thermal energy applied in creating the lesion, and transforming the solved model into the spatial pattern of MRI pixel values;
      matching the MRI image with the spatial pattern of MRI pixel values; and
      finding a local maximum value in the matched MRI image; and
   a memory, which is configured to store the MRI image with a location, wherein a location of the local maximum value marked thereon as the location of the lesion.

8. The system according to claim 7, wherein the processor is further configured to normalize the spatial pattern of pixel values, after transforming the solved model.

9. The system according to claim 7, wherein the processor is configured to match the MRI image with the spatial pattern of pixel values by convolving the MRI image with the spatial pattern of pixel values.

10. The system according to claim 7, wherein the processor is configured to match the MRI image with the spatial pattern of pixel values by matching a segmented region of the MRI image.

11. The system according to claim 7, wherein the processor is further configured to save the matched MRI image in the memory.

* * * * *